(12) United States Patent
Fiore et al.

(10) Patent No.: US 7,300,912 B2
(45) Date of Patent: Nov. 27, 2007

(54) FOAMING CLEANSING PREPARATION AND SYSTEM COMPRISING COATED ACID AND BASE PARTICLES

(76) Inventors: Robert A. Fiore, 12 Alden Rd., West Yarmouth, MA (US) 02673; Samuel J. Huang, 176 Windham Rd., Hampton, CT (US) 06247

( * ) Notice: Subject to any disclaimer, the term of this patent is extended or adjusted under 35 U.S.C. 154(b) by 30 days.

(21) Appl. No.: 11/201,566

(22) Filed: Aug. 10, 2005

(65) Prior Publication Data
US 2007/0037727 A1    Feb. 15, 2007

(51) Int. Cl.
C11D 3/10    (2006.01)
C11D 9/26    (2006.01)

(52) U.S. Cl. .................. 510/349; 510/117; 510/119; 510/130; 510/135; 510/349; 510/438; 510/441; 510/446; 510/477; 510/478; 510/509

(58) Field of Classification Search ............ 510/117, 510/119, 130, 135, 349, 438, 441, 446, 477, 510/478, 509
See application file for complete search history.

(56) References Cited

U.S. PATENT DOCUMENTS

| | | | |
|---|---|---|---|
| 2,879,231 A | 3/1959 | Allan et al. | |
| 2,995,521 A | 8/1961 | Estignard-Bluard | |
| 3,541,581 A | 11/1970 | Monson | |
| 3,980,091 A | 9/1976 | Dasher et al. | |
| 4,294,728 A | 10/1981 | Vanlerberghe et al. | |
| 4,405,489 A | 9/1983 | Sisbarro | |
| 4,417,993 A * | 11/1983 | Gergely ................. | 510/117 |
| 4,678,661 A * | 7/1987 | Gergely et al. ............ | 424/44 |
| 4,726,944 A | 2/1988 | Osipow et al. | |
| 4,744,979 A | 5/1988 | Osipow et al. | |
| 4,772,427 A | 9/1988 | Dawson et al. | |
| 4,871,530 A | 10/1989 | Grollier et al. | |
| 4,942,038 A | 7/1990 | Wallach | |
| 5,037,818 A | 8/1991 | Sime | |
| 5,085,857 A | 2/1992 | Reid et al. | |
| 5,124,081 A | 6/1992 | Vanlerberghe et al. | |
| 5,186,857 A | 2/1993 | Ramirez et al. | |
| 5,198,470 A | 3/1993 | Zysman et al. | |
| 5,330,758 A | 7/1994 | Hansenne-Richoux et al. | |
| 5,336,665 A | 8/1994 | Garner-Gray et al. | |
| 5,354,564 A | 10/1994 | Borish et al. | |
| 5,510,120 A | 4/1996 | Jones et al. | |
| 5,514,369 A | 5/1996 | Salka et al. | |
| 5,518,736 A | 5/1996 | Magdassi et al. | |
| 5,591,449 A | 1/1997 | Bollens et al. | |
| 5,599,531 A | 2/1997 | Holcomb | |
| 5,658,575 A | 8/1997 | Ribier et al. | |
| 5,660,839 A | 8/1997 | Allec et al. | |
| 5,660,853 A | 8/1997 | Hansenne-Richoux | |
| 5,667,800 A | 9/1997 | De Vringer | |
| 5,741,518 A | 4/1998 | Ribier et al. | |
| 5,753,241 A | 5/1998 | Ribier et al. | |
| 5,759,526 A | 6/1998 | Simonnet et al. | |
| 5,773,611 A | 6/1998 | Zysman et al. | |
| 5,780,060 A | 7/1998 | Levy et al. | |
| 5,785,891 A | 7/1998 | Lim | |
| 5,814,343 A | 9/1998 | Jones et al. | |
| 5,824,629 A * | 10/1998 | Petritsch ................ | 510/120 |
| 5,851,517 A | 12/1998 | Mougin et al. | |
| 5,874,105 A | 2/1999 | Watkins et al. | |
| 5,885,564 A | 3/1999 | Zastrow et al. | |
| 5,912,012 A * | 6/1999 | Carlin et al. ............ | 424/464 |
| 5,919,487 A | 7/1999 | Simonnet et al. | |
| 5,925,364 A | 7/1999 | Ribier et al. | |
| 5,945,095 A | 8/1999 | Mougin et al. | |
| 6,010,707 A | 1/2000 | Philippe et al. | |
| 6,013,618 A | 1/2000 | Morelli et al. | |
| 6,015,574 A | 1/2000 | Cannell et al. | |
| 6,039,936 A | 3/2000 | Restle et al. | |
| 6,042,792 A | 3/2000 | Shefer et al. | |
| 6,048,520 A | 4/2000 | Hoshowski | |
| 6,063,390 A * | 5/2000 | Farrell et al. ............ | 424/404 |
| 6,066,328 A | 5/2000 | Ribier et al. | |
| 6,071,535 A | 6/2000 | Hayward et al. | |
| 6,083,899 A | 7/2000 | Baker et al. | |
| 6,087,311 A * | 7/2000 | Van Dijk ................ | 510/294 |
| 6,087,322 A | 7/2000 | Morelli et al. | |
| 6,090,401 A | 7/2000 | Gowan, Jr. et al. | |
| 6,126,948 A | 10/2000 | Simonnet et al. | |
| 6,156,826 A | 12/2000 | Guenin et al. | |
| 6,200,964 B1 | 3/2001 | Singleton et al. | |

(Continued)

FOREIGN PATENT DOCUMENTS

CA    1021264    11/1977

(Continued)

Primary Examiner—Charles Boyer

(57) ABSTRACT

A foaming cleansing preparation and system that produce a high quality, self-sustaining foam immediately upon exposure to water without physical agitation or rubbing is provided. The inventive cleansing preparation is made up of at least one dry acid, at least one dry base, and at least one liquid film-forming cleansing agent. When the cleansing preparation is exposed to water, the acid(s) and the base(s) will react to form a gas and the cleansing agent(s) will form a liquid film, and the gas and the liquid film will then interact to form or generate a foam. The inventive cleansing system is made up of a plurality of delivery particles, with each such delivery particle containing one or more components of the inventive cleansing preparation.

10 Claims, No Drawings

U.S. PATENT DOCUMENTS

| | | |
|---|---|---|
| 6,210,656 B1 | 4/2001 | Touzan et al. |
| 6,235,318 B1 | 5/2001 | Lombardy, Jr. et al. |
| 6,258,343 B1 | 7/2001 | Kiczek, Sr. et al. |
| 6,310,014 B1 * | 10/2001 | Rau ........................... 510/108 |
| 6,333,024 B1 * | 12/2001 | Masters et al. ................ 424/49 |
| 6,352,689 B1 | 3/2002 | Szymczak |
| 6,376,450 B1 * | 4/2002 | Ghosh et al. ................ 510/392 |
| 6,432,450 B1 * | 8/2002 | Gergely et al. ............. 424/489 |
| 6,440,923 B1 | 8/2002 | Lyle et al. |
| 6,491,902 B2 | 12/2002 | Shefer et al. |
| 6,583,103 B1 * | 6/2003 | Klinkhammer ............. 510/478 |
| 6,627,185 B2 | 9/2003 | Kumar et al. |
| 6,627,585 B1 | 9/2003 | Steer |
| 6,645,525 B1 | 11/2003 | Woiszwillo |
| 6,660,282 B2 | 12/2003 | Crotty et al. |
| 6,682,726 B2 | 1/2004 | Marchesi et al. |
| 6,699,828 B1 * | 3/2004 | de Buzzaccarini et al. .. 510/372 |
| 6,774,179 B2 | 8/2004 | Ferritto et al. |
| 6,939,841 B2 * | 9/2005 | Requejo ..................... 510/446 |
| 7,056,877 B2 * | 6/2006 | Caswell et al. ............. 510/439 |
| 2002/0166779 A1 * | 11/2002 | Etesse et al. ................ 206/219 |
| 2002/0194684 A1 * | 12/2002 | Wiesche et al. ................ 8/405 |
| 2005/0042261 A1 * | 2/2005 | Hasenoehrl et al. ........ 424/443 |

FOREIGN PATENT DOCUMENTS

| | | |
|---|---|---|
| EP | 386898 | 9/1993 |
| GB | 1444334 | 7/1976 |
| WO | WO95/05158 | 2/1995 |
| WO | WO95/22311 | 8/1995 |

* cited by examiner

FOAMING CLEANSING PREPARATION AND SYSTEM COMPRISING COATED ACID AND BASE PARTICLES

FIELD OF THE INVENTION

The present invention generally relates to a foaming cleansing preparation and system, and more particularly relates to a cleansing preparation and system that produce a high quality, self-sustaining foam immediately upon exposure to water without physical agitation or rubbing.

BACKGROUND AND SUMMARY OF THE INVENTION

Conventional shampoos typically comprise water and a dispersed or solubilized surface-active agent (e.g., a soap or detergent, a surfactant, or a combination of these agents). They may also include ingredients such as foam builders, foam stabilizers, emollients, viscosity modifiers, lubricants, humectants, preservatives, and fragrance. These shampoos are applied to the hair of the user and, in the course of such application; the shampoo is worked in a fashion that causes the shampoo to foam. The foams produced by these so-called "post-foaming" shampoos are relatively weak foams that quickly flatten.

Instant foaming shampoos are also known and typically comprise a propellant or blowing agent in addition to the above-named ingredients. They are dispensed from pressurized aerosol containers in the form of a rich foam lather for spreading by hand on the area to be cleaned. The foams produced by these instant foaming shampoos are also relatively weak, and deflate relatively quickly because of larger-sized bubbles, lower quality foam, and because the foaming action is not self-sustaining after dispensing.

It has now been found that the aforementioned problems and limitations of previous foaming shampoos are overcome by the present cleansing preparation which produces a high quality and self-sustaining foam immediately upon exposure to water without the need for physical agitation or rubbing.

Generally speaking, the present invention provides a cleansing preparation that foams upon contact with water, which comprises:
   (a) at least one dry acid;
   (b) at least one dry base; and
   (c) at least one liquid film-forming cleansing agent,
   wherein, when the cleansing preparation is exposed to water, the acid(s) and the base(s) will react to form a gas and the cleansing agent(s) will form a liquid film, the gas and the liquid film will then interact to form or generate a foam (i.e., a mass of gas bubbles in a matrix of liquid film).

The present invention also provides a cleansing system which comprises a plurality of delivery particles, with each such delivery particle containing one or more of the above-named components of the inventive cleansing preparation, wherein, when the delivery particles are exposed to water, the particles will dissolve or break apart thereby releasing at least the acid(s) and the base(s). As noted above, the acid(s) and the base(s) will then react to form a gas, while the cleansing agent(s) will form a liquid film. The interaction of the gas and the liquid film will cause the formation or generation of a foam.

Other features and advantages of the invention will be apparent to one of ordinary skill from the following detailed description. Unless otherwise defined, all technical and scientific terms used herein have the same meaning as commonly understood by one of ordinary skill in the art to which this invention belongs. All publications, patent applications, patents and other references mentioned herein are incorporated by reference in their entirety. In case of conflict, the present specification, including definitions, will control. In addition, the materials, methods, and examples are illustrative only and not intended to be limiting.

BEST MODE FOR CARRYING OUT THE INVENTION

The cleansing preparation of the present invention may be used in personal care products such as hair shampoos, hair conditioners, mousses, skin cleansers (e.g., acne cleansers, body wash, cosmetic cleansers, facial cleansers, surgical scrubs), depilatory preparations, and shaving preparations. The inventive cleansing preparation can also be used in animal care products, household cleaning products such as universal detergents (e.g., fabric cleansers, automobile and equipment cleansers), fire suppression products, and the like.

The inventive preparation produces a multitude of small bubbles or foam over a period of time. The foam is a high-quality, long-lasting foam that provides the user with a pleasing effervescent effect.

As noted above, the cleansing preparation of the present invention foams upon contact with water, and basically comprises:
   (a) at least one dry acid;
   (b) at least one dry base; and
   (c) at least one liquid film-forming cleansing agent.

When exposed to water, the acid(s) and the base(s) will react to form a gas, while the cleansing agent(s) will form a liquid film. The interaction of the gas and the liquid film causes the formation of a foam.

Dry acids suitable for use in the present invention include, but are not limited to, ascorbic acid, boric acid, citric acid, lactic acid, mucic acid, sorbic acid, tartaric acid, acids derived from sugars (e.g., D-glucaric acid, D-glucuronic acid), acid-salts derived from multi-functional acids (e.g., boric acid, carbonic acid, citric acid, phosphoric acid, sulfuric acid, tartaric acid) where the acidic hydrogen ion(s) has been partially replaced by a cation(s) (e.g., aluminum ion, ammonium ion, calcium ion, potassium ion, sodium ion), and combinations thereof. Preferably, the dry acid(s) dissolves rapidly in water, and more preferably is dry boric acid, dry citric acid, or dry tartaric acid, which are available from a number of chemical supply houses including, but not limited to, Fisher Chemicals, 1 Reagent Lane, Fairlawn, N.J. 07410 ("Fisher Chemicals").

The dry acid(s) is present in the inventive cleansing preparation in amounts ranging from about 1 to about 50% by dry weight (preferably, from about 5 to about 45% by dry weight, and more preferably, from about 10 to about 40% by dry weight), based on the total dry weight of the cleansing preparation.

Dry bases suitable for use in the present invention include, but are not limited to, carbonates (e.g., sodium carbonate), bicarbonates (e.g., sodium bicarbonate), N-carboxylates of ammonium, sodium or potassium, and combinations thereof. Preferably, the dry base(s) is sodium carbonate or sodium bicarbonate, which are available from, for example, Fisher Chemicals.

The dry base(s) is present in the inventive cleansing preparation in amounts ranging from about 1 to about 50% by dry weight (preferably, from about 5 to about 45% by dry weight, and more preferably, from about 10 to about 40% by dry weight), based on the total dry weight of the cleansing preparation.

The term "dry", as used herein, is intended to mean essentially free of water (i.e., acids or bases containing less than 1% by weight water, based on the total weight of the acid or base).

Liquid film-forming cleansing agents suitable for use in the present invention include, but are not limited to, ionic (cationic, anionic, zwitterionic) surfactants, nonionic (neutral) surfactants, and amphoteric surfactants, alkaline surfactants, and neutral surfactants.

In a preferred embodiment, the liquid film-forming cleansing agent(s) is selected from the group of betaines, carboxylates (e.g., sodium carboxylates), polyalkylene oxides, alkyl polyglycosides, alkyl saccharides, sulfates, alkyl sulfonates (e.g., sodium alkyl sulfonates including sodium dodecyl sulfonate), alkylaryl sulfonates (e.g., sodium alkylaryl sulfonates), alkyl benzene sulphonates, and combinations thereof. In a more preferred embodiment, the liquid film-forming cleansing agent(s) is sodium dodecyl sulfonate, which is available from, for example, Fisher Chemicals.

The liquid film-forming cleansing agent(s) is present in the inventive cleansing preparation in an amount ranging from about 1 to about 20% by dry weight (preferably, from about 1 to about 10% by dry weight), based on the total dry weight of the cleansing preparation.

The inventive cleansing preparation may also contain one or more additional components including, but not limited to, aesthetic additives such as fragrance and/or colorants or dyes (e.g., blue dye colorant), burst agents, chelating agents (e.g., ethylenediaminetetraacetic acid (EDTA), acetoacetone) to remove metals and soften water, emollients and/or humectants, foam enhancers (e.g., dihydric alcohol, glycerin, poly(vinyl alcohol), poly(N-vinylpyrrolidone)), hair and skin conditioners (e.g., hydrophilic polymers including, but not limited to, cellulose materials such as alkylcellulose, hydroxyalkylcellulose and carboxyalkylcellulose, hyaronic acid, natural protein such as gelatin, natural polysaccharide such as chitosan, polyacrylamide, polyacrylate, poly(amino acid), polyenols, polymethacrylates, poly(N-vinylpyrrolidone), polypeptides, poly(ethylene glycol), poly(ethylene oxide), poly(vinyl alcohol), and derivatives and combinations thereof), hair and skin moisturizers, preservatives, and viscosity adjusters and/or feel enhancers, provided that any such additional component(s) does not serve to adversely impact upon the desirable properties of the cleansing preparation.

As will be readily appreciated by those skilled in the art, these additional components may be added as necessary and at concentrations for consumer acceptance. By way of example, the inventive cleansing preparation may include from about 0.1 to about 5% by dry weight (preferably, from about 0.1 to about 1% by dry weight), based on the total dry weight of the cleansing preparation, of fragrance, colorant or dye, or combinations thereof. By way of further example, the inventive cleansing preparation may include from about 1 to about 5% by dry weight (preferably, from about 2 to about 4% by dry weight), based on the total dry weight of the cleansing preparation, of one or more hair and skin conditioners.

In a preferred embodiment, the cleansing preparation of the present invention comprises:

(a) from about 1 to about 50% by dry weight of dry citric acid;

(b) from about 1 to about 50% by dry weight of dry sodium carbonate or dry sodium bicarbonate;

(c) from about 1 to about 20% by dry weight of sodium dodecyl sulfonate surfactant; and (d) from about 0.1 to about 5% by dry weight of a fragrance and a blue dye colorant.

Upon exposure to water, the dry citric acid and the dry sodium carbonate or sodium bicarbonate will react to form carbon dioxide ($CO_2$), with foaming preferably commencing within 10 seconds after water exposure, and ending after about 120 seconds. As will be readily appreciated by those skilled in the art, preferred pH ranges for these aqueous solutions range from about 4 to about 9.

In another preferred embodiment contemplated by the present invention, the cleaning preparation further comprises from about 1 to about 5% by dry weight, based on the total dry weight of the cleansing preparation, of one or more hair and skin conditioners. The hair and skin conditioner(s) may be added to the cleaning preparation in particle, coated particle, or encapsulated particle (i.e., core/shell) form. The one or more hair and skin conditioners are formulated, coated, or encapsulated so as to completely dissolve only after the cleansing action of the inventive preparation has concluded (i.e., from about 10 to about 30 seconds after initial water exposure).

The inventive cleansing preparation may be delivered to a target site by way of any suitable delivery means. In one contemplated embodiment, the inventive cleansing preparation is conveyed to the target site in particles that contain the above-named components. These so-called "delivery" particles may in turn be contained or suspended in a non-aqueous dispensing medium such as an aerosol spray formulation, a viscous fluid, a gel, or a dry paste.

Referring now to the cleansing system of the present invention, this system comprises a plurality of delivery particles, with each delivery particle containing one or more components of the inventive cleansing preparation. When the delivery particles are exposed to water, the particles will dissolve or break apart thereby releasing the dry acid(s) and the dry base(s), allowing them to react to form a gas, while the liquid film-forming cleansing agent(s) forms a liquid film, which will in turn interact with the gas formed by the acid(s) and the base(s), causing the formation or generation of a foam. The inventive system may further comprise additional components (e.g., aesthetic additives such as fragrance and/or colorants or dyes) in liquid, powder, granular or agglomerate form.

The delivery particles contemplated by the present invention, which serve to encapsulate at least some of the cleansing preparation components, fall into two main categories: those in which at least some of the components are surrounded by a wall or barrier (i.e., core-shell delivery particles); and those in which at least some of the components are encapsulated in a material matrix (e.g., gel type delivery particles). As noted above, the delivery particles will release the components disposed therein upon being exposed to a water environment.

The dry acid and dry base components of the inventive cleansing preparation may be separately placed or contained within the delivery particles, or may be placed together within a particle.

In one contemplated embodiment, the inventive core-shell delivery particles comprise a core portion made up of the dry acid(s) or the dry base(s), and a shell portion or coating made up of the liquid film-forming cleansing agent(s), or a mixture of the cleansing agent(s) and one or more hair and skin conditioners (e.g., sodium dodecyl sulfonate, or mixtures of sodium dodecyl sulfonate and poly(ethylene glycol), poly(vinyl alcohol), or poly(N-vinylpyrrolidone). Suitable dry acid(s), dry base(s), liquid film-forming cleansing agent(s), and hair and skin conditioner(s) are as described above.

The shell portion or coating of the inventive core-shell delivery particles serves to not only contain the named components, but also to decrease the rate of dissolution or bursting, thereby delaying release of the components, and to reduce or prevent agglomeration. Preferred shell portion or coating thicknesses range from about 1 to about 100 microns.

The size of the core-shell delivery particles used in the present invention may range from about 1 micron to about 1000 microns in diameter, and preferably range from about 10 microns to about 200 microns in diameter.

For those embodiments of the core-shell delivery particles where the dry acid(s) and the dry base(s) are housed together within the core portion of the particle, the dry acid(s) and the dry base(s) must be isolated to prevent premature reaction. This may be accomplished by, for example, coating each such component with one of the above-named liquid film-forming cleansing agents or hair and skin conditioners. More specifically, the dry acid and dry base components may be provided with an outer or exterior coating, which may be prepared at coating thicknesses ranging from about 1 to about 100 microns. Such coatings may be used to isolate and decrease the rate of hydration or rehydration of the components, thereby preventing premature reaction of the acid(s) and the base(s), and/or possible agglomeration.

In one such preferred embodiment, the core-shell delivery particles each comprise: a core portion made up of from about 40 to about 60% by dry weight of dry citric acid coated with poly(ethylene glycol), and from about 60 to about 40% by dry weight of dry sodium carbonate or sodium bicarbonate coated with poly(ethylene glycol); and a shell portion made up of either sodium dodecyl sulfonate, or a mixture of sodium dodecyl sulfonate and poly(ethylene glycol), poly(vinyl alcohol), or poly(N-vinylpyrrolidone).

The cleansing system of the present invention may condition as well as cleanse a target surface. In one such contemplated embodiment, the cleansing system is made up of core-shell delivery particles that comprise: core portions made up of either the dry acid(s), the dry base(s), or the hair and skin conditioner(s) (e.g., hydrophilic polymers), each core component being encapsulated within a shell portion made up of the liquid film-forming cleansing agent(s) (e.g., sodium dodecyl sulfonate), or a mixture of the cleansing agent(s) and one or more hair and skin conditioners (e.g., mixtures of sodium dodecyl sulfonate and poly(ethylene glycol), poly(vinyl alcohol), or poly(N-vinylpyrrolidone). The thickness of each shell portion encapsulating a hair and skin conditioner(s) may be greater than the thickness of the shell portions encapsulating the acid and the base components so as to provide for delayed dissolution and thus delayed release (i.e., from about 10 seconds to about 5 minutes from the release time for the dry acid and dry base components) of the hair and skin conditioner(s). The compositions used to prepare the shell portions for each core component may also be formulated to control the dissolution time.

In a preferred embodiment of the inventive cleansing/conditioning system, the system comprises:

(a) from about 1 to about 50% by dry weight, based on the total dry weight of the delivery particles, of dry tartaric acid—sodium dodecyl sulfonate core-shell delivery particles;

(b) from about 1 to about 50% by dry weight, based on the total dry weight of the delivery particles, of dry sodium carbonate or dry sodium bicarbonate—sodium dodecyl sulfonate core-shell delivery particles;

(c) from about 0.1 to about 5% by dry weight, based on the total dry weight of the delivery particles, of a fragrance and a blue dye colorant; and (d) from about 1 to about 20% by dry weight, based on the total dry weight of the delivery particles, of poly(N-vinylpyrrolidone)—sodium dodecyl sulfonate core-shell delivery particles.

As will be readily appreciated by those skilled in the art, the inventive system allows for the simultaneous use of both anionic cleansing agents or surfactants and cationic conditioning agents by, for example, coating these components, or placing these components in separate delivery particles, thereby avoiding undesirable reaction.

The encapsulated delivery particles of the present invention may be prepared using conventional encapsulation methods and techniques such as solution coating and multi-solvent encapsulation processes.

The inventive gel type delivery particles are prepared using suitable gel or gel type materials, which include, but are not limited to, hydrogels such as poly-(2-hydroxyethylmethacrylate), polyacrylamide, poly(vinyl alcohol), poly(N-vinylpyrrolodone), chitosan, gelatin, copolymers containing one or more of these gel or gel-type materials, and mixtures or combinations thereof. Preferably, the gel or gel type material(s) is polyacrylamide gel.

The gel or gel type material is typically present in an amount ranging from about 1 to about 10% by dry weight (preferably, from about 1 to about 5% by dry weight) of the gel type delivery particle.

Some or all of the gel type delivery particles may be provided with an outer or exterior coating, such as gelatin or poly(ethylene oxide), at coating thicknesses ranging from about 1 to about 100 microns. Such coatings may be used to decrease the rate of dissolution, thereby delaying release of some or all of the named components. Such coatings may also be used to prevent agglomeration.

The size of the gel type delivery particles used in the present invention may range from about 1 micron to about 1000 microns in diameter, and preferably range from about 50 microns to about 200 microns in diameter.

In one embodiment contemplated by the present invention, the gel type delivery particles each comprise: from about 1 to about 50% by dry weight of dry citric acid; from about 1 to about 50% by dry weight of dry sodium carbonate or dry sodium bicarbonate; from about 1 to about 20% by dry weight of sodium dodecyl sulfonate surfactant; and from about 0.1 to about 5% by dry weight of a fragrance and a blue dye colorant, suspended in from about 1 to about 10% by dry weight polyacrylamide gel.

As noted above, the delivery particles of the present invention may be contained or suspended in a non-aqueous dispensing medium such as an aerosol spray formulation, a viscous fluid, a gel, or a dry paste and conveyed to a target site. The delivery particles remain intact in the dispensing medium over prolonged storage and retain most of the components. However, once the dispensing medium is exposed to water, the dispensing medium will evaporate or dissolve in water and the delivery particles will dissolve or break apart, thereby releasing the components. Foaming and bubbling action will commence in less than about 5 seconds and may last in excess of 3 minutes, and will preferably commence in less than about 10 seconds, preferably lasting up to about 120 seconds.

In a preferred embodiment, the delivery particles are contained or suspended in compressed air in an aerosol container.

While various embodiments of the present invention have been described above, it should be understood that they have been presented by way of example only, and not limitation. Thus, the breadth and scope of the present invention should not be limited by any of the exemplary embodiments.

The invention claimed is:

1. A cleansing system that foams upon contact with water and that comprises a plurality of delivery particles, wherein each delivery particle contains one or more components selected from the group consisting of dry acids, dry bases, and film-forming cleansing agents, wherein when a delivery particle contains both dry acid(s) and dry base(s), the acid(s) and the base(s) are not in direct contact with each other, and wherein the plurality of delivery particles are core-shell delivery particles that each comprise: a core portion made of one or more optionally coated components selected from the group consisting of dry acids, dry bases, and hair and skin conditioners; and a shell portion made of one or more components selected from the group consisting of film-forming cleansing agents, and mixtures of film-forming cleansing agents and hair and skin conditioners, and wherein when the delivery particles are exposed to water, the particles will dissolve or break apart thereby releasing the components contained therein, the released acids(s) and the released bases(s) will then react to form a gas and the cleansing agents(s) will form a liquid film, and the gas and the liquid film will then interact to form or generate a foam.

2. The cleansing system of claim 1, wherein the core portion of each core-shell delivery particle is made up of dry acids and dry bases that are coated with one or more hair and skin conditioners.

3. The cleansing system of claim 1, wherein the core portion of each core-shell delivery particle is made up of from about 40 to about 60% by dry weight of dry citric acid coated with poly(ethylene glycol), from about 60 to about 40% by dry weight of dry sodium carbonate or sodium bicarbonate coated with poly(ethylene glycol); and wherein the shell portion is made up of sodium dodecyl sulfonate, or a mixture of sodium dodecyl sulfonate and poly(ethylene glycol), poly(vinyl alcohol), or poly(N-vinylpyrrolidone).

4. The cleansing system of claim 1, wherein the plurality of delivery particles each comprise one or more components selected from a group consisting of dry acids, dry barn, film-forming cleansing agents, aesthetic additives, and hair and skin conditioners, encapsulated in a gel.

5. The cleansing system of claim 1, wherein at least one dry acid is selected from the group consisting of ascorbic acid, boric acid, citric acid, lactic acid, mucic acid, sorbic acid, tartaric acid, acids derived from sugars, acid-salts derived from multi-functional acids where at least one acidic hydrogen ion has been partially replaced by at least one cation, and combinations thereof.

6. The cleansing system of claim 1, wherein at least one dry base is selected from the group consisting of carbonates, bicarbonates, N-carboxylates of ammonium, sodium or potassium, and combinations thereof.

7. The cleansing system of claim 1, wherein at least one film-forming cleansing agent is a surfactant.

8. The cleansing system of claim 7, wherein at least one film-forming cleansing agent is selected from the group consisting of betaines, carboxylates, polyalkylene oxides, alkyl polyglycosides, alkyl saccharides, sulfates, alkyl sulfonates, alkylaryl sulfonates, alkyl benzene sulfonates, and combinations thereof.

9. A cleansing system that foams upon contact with water and that comprises a mixture of coated dry acid panicles and coated dry base particles, wherein each particle is coated with one or more components selected from the group consisting of film-forming cleansing agents, and mixtures of film-forming cleansing agents and hair and skin conditioners, and wherein when the coated particles are exposed to water, the coatings will dissolve or the coated particles will break apart, thereby releasing the acid(s) or base(s) contained therein, the released acid(s) and the released base(s) will then react to form a gas, the cleansing agent(s) will form a liquid film, and the gas and the liquid film will then interact to form or generate a foam.

10. A cleansing system that foams upon contact with water and that comprises a plurality of core-shell delivery particles, wherein each core-shell delivery particle comprises: a core portion made up of from about 40 to about 40% by dry weight of dry citric acid coated with poly(ethylene glycol) and from about 40 to about 40% by dry weight of dry sodium carbonate or sodium bicarbonate coated with poly(ethylene glycol); and a shell portion made up of sodium dodecyl sulfonate, or a mixture of sodium dodecyl sulfonate and poly(ethylene glycol), poly(vinyl alcohol), or poly(N-vinylpyrrolidone), wherein when the delivery particles are exposed to water, the particles will dissolve or break apart thereby releasing the components contained therein, the released acid(s) and the released base(s) will then react to form a gas and the sodium dodecyl sulphonate or mixture containing sodium dodecyl sulfonate will form a liquid film, and the gas and the liquid film will then interact to form or generate a foam.

* * * * *

UNITED STATES PATENT AND TRADEMARK OFFICE
CERTIFICATE OF CORRECTION

PATENT NO. : 7,300,912 B2  Page 1 of 1
APPLICATION NO. : 11/201566
DATED : November 27, 2007
INVENTOR(S) : Robert Fiore et al.

It is certified that error appears in the above-identified patent and that said Letters Patent is hereby corrected as shown below:

Column 7, Line 46,
"dry barn" should read -- dry bases --.

Column 8, Line 19,
"coated dry acid panicles" should read -- coated dry acid particles --.

Column 8, Line 34,
"a core portion made up of from about 40 to about" should read -- a core portion made up of from about 10 to about --.

Column 8, Line 36,
"and from about 40 to about 40% by dry" should read -- and from about 10 to about 40% by dry --

Signed and Sealed this

Thirtieth Day of December, 2008

JON W. DUDAS
*Director of the United States Patent and Trademark Office*